(12) United States Patent
Edwards et al.

(10) Patent No.: US 9,452,124 B2
(45) Date of Patent: Sep. 27, 2016

(54) ORAL CARE COMPOSITION FOR ENHANCING DELIVERY OF ACTIVE AGENTS TO MUCOSA/SOFT ORAL TISSUE AND TOOTH SURFACES IN THE ORAL CAVITY

(71) Applicant: Glaxo Group Limited, Brentford, Middlesex (GB)

(72) Inventors: Mark Ieuan Edwards, Surrey (GB); Simon King, Surrey (GB); Nisha Patel, Surrey (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 14/364,692

(22) PCT Filed: Dec. 11, 2012

(86) PCT No.: PCT/EP2012/075082
§ 371 (c)(1),
(2) Date: Jun. 12, 2014

(87) PCT Pub. No.: WO2013/087623
PCT Pub. Date: Jun. 20, 2013

(65) Prior Publication Data
US 2015/0004105 A1   Jan. 1, 2015

(30) Foreign Application Priority Data
Dec. 12, 2011   (GB) .................................. 1121300.6

(51) Int. Cl.
| | | |
|---|---|---|
| *A61K 47/38* | (2006.01) | |
| *A61Q 11/00* | (2006.01) | |
| *A61K 33/16* | (2006.01) | |
| *A61K 8/73* | (2006.01) | |
| *A61K 8/27* | (2006.01) | |
| *A61K 8/34* | (2006.01) | |
| *A61K 8/21* | (2006.01) | |
| *A61K 8/37* | (2006.01) | |
| *A61K 8/49* | (2006.01) | |
| *A61K 8/92* | (2006.01) | |
| *A61K 8/19* | (2006.01) | |

(52) U.S. Cl.
CPC .................. *A61K 8/731* (2013.01); *A61K 8/19* (2013.01); *A61K 8/21* (2013.01); *A61K 8/27* (2013.01); *A61K 8/345* (2013.01); *A61K 8/347* (2013.01); *A61K 8/37* (2013.01); *A61K 8/4926* (2013.01); *A61K 8/922* (2013.01); *A61Q 11/00* (2013.01); *A61K 2800/40* (2013.01)

(58) Field of Classification Search
CPC .. A61K 2300/00; A61K 9/2054; A61K 8/69; A61Q 11/00
See application file for complete search history.

(56) References Cited

U.S. PATENT DOCUMENTS

| | | | | |
|---|---|---|---|---|
| 5,188,821 A | * | 2/1993 | Gaffar et al. | 424/52 |
| 5,328,682 A | * | 7/1994 | Pullen et al. | 424/49 |
| 5,487,898 A | * | 1/1996 | Lu et al. | 424/435 |
| 6,117,417 A | * | 9/2000 | Wicks et al. | 424/54 |
| 2009/0068122 A1 | * | 3/2009 | Pilch et al. | 424/52 |

* cited by examiner

*Primary Examiner* — Frederick Krass
*Assistant Examiner* — Tracy Liu
(74) *Attorney, Agent, or Firm* — Nora L. Stein; Theodore R. Furman

(57) ABSTRACT

Oral care compositions comprising one or more active agents and hydroxypropyl cellulose, and that are liquid at or below room temperature and which form a two-phase cloudy system at body temperature. In certain embodiments the active agent is a mineralizing agent, an anti-caries agent, an anti-inflammatory agent, an antibacterial agent, an anti-fungal agent, an anti-malodour agent or a mixture thereof.

9 Claims, No Drawings

ORAL CARE COMPOSITION FOR ENHANCING DELIVERY OF ACTIVE AGENTS TO MUCOSA/SOFT ORAL TISSUE AND TOOTH SURFACES IN THE ORAL CAVITY

This application is a 371 of International Application No. PCT/EP2012/075082, filed Dec. 11, 2012, which claims the priority of GB Application No. GB 1121300.3 filed Dec. 12, 2011, which is incorporated herein in its entirety.

FIELD OF THE INVENTION

The present invention relates to oral care compositions comprising one or more active agents and hydroxypropyl cellulose which enhances delivery of the active agent to mucosa/soft oral tissue and tooth surfaces in the oral cavity. In certain embodiments the active agent is a mineralizing agent, an anti-caries agent, an anti-inflammatory agent, an antibacterial agent, an antifungal agent, an anti-malodour agent or a mixture thereof.

BACKGROUND OF THE INVENTION

Oral care compositions such as mouthwashes, dentifrices and the like often contain active agents for use, for example, in protecting against cavities, plaque, gum problems, tartar build-up and malodour. Measures for enhancing the delivery of such actives, with a view to improving their effectiveness, have been proposed in the art.

For example, GB 1 290 627 (Unilever Ltd) describes the use of sparingly soluble salts of zinc as a means of delivering zinc ions to the oral cavity for use against calculus and plaque on a tooth surface. According to GB 1 290 627 the sparingly soluble zinc salts have another important attribute: they can provide a "reservoir" effect in the mouth. Since the compounds are only slowly dissolved in saliva, they can become lodged in cracks, crevices and interstices between the teeth as well as in dental plaque and other deposits. The zinc ions are released gradually over a period of time, promoting longevity of action against plaque and calculus.

EP 0 434 284 B1 (Johnson & Johnson Consumer Products Inc.) also seeks to provide a source of (bioavailable) zinc ions for use in oral care. According to EP 0 434 281, this is achieved by the use of an aqueous liquid mouthwash composition of a zinc salt including a pharmaceutically acceptable zinc salt codissolved with a complexing agent selected from the group consisting of sodium gluconate, maleic acid, aspartic acid, gluconic acid, succinic acid, glucuronic acid, sodium glutamate and fumaric acid, in a naturally derived anionic polymer of sodium carboxymethylcellulose or sodium alginate, the composition having a pH of from 5.7 to 6.5.

EP 0 558 586 B1 (Pharmacia AB) discloses that certain water-soluble non-ionic cellulose ethers in combination with a charged surfactant in water have the property of being liquid at room temperature and forming a gel when warmed to body temperature. Such properties can be used for specialized drug delivery. EP 0 558 586 B1 discloses that when a mouth rinse solution, according to the invention therein, contains a suitable anionic surfactant it is possible to incorporate fluoride ions for anti-caries treatment. After being warmed up in the mouth the solution is transformed to a gel which sticks to the mucous membrane in a thin layer. The gel then provides a source of fluoride ions which are slowly released to the saliva.

GB 2 235 133A (Colgate-Palmolive Company) discloses that the anti-plaque effectiveness of an antibacterial agent such as 2,4,4'-trichloro-2'-hydroxyldiphenyl ether (triclosan) is enhanced by the use of an antibacterial-enhancing agent (AEA). Suitable AEAs are disclosed as including anionic polymers such as maleic acid-methyl vinyl ether copolymer or a polymer containing phosphonic groups. According to GB 2 235 133A the AEA contains at least one delivery enhancing group and at least one organic retention-enhancing group or preferably a plurality of both groups.

U.S. Pat. No. 5,496,541 (Pilot Research & Development Co) relates to dental products containing a ternary surfactant system. According to U.S. Pat. No. 5,496,541 excellent adhesion to tooth surfaces and oral mucosa is achieved by the use of a poloxamer-anionic polysaccharide-nonionic cellulose ether surfactant system, which enhances the beneficial effects of the surfactant system and of the other active ingredients in the formulation.

According to EP 0 864 315B1 (Sunstar Inc.), measures for enhancing the adhesive properties of preparations containing a drug (a cationic bactericide) have been proposed in the art for improving the effectiveness of the bactericide. A generally employed technique for improving the adhesion of a preparation to wet surfaces e.g. the mucous membrane in the oral cavity, is described as incorporating in the preparation a carboxyvinyl polymer, polyacrylic acid, or an analogue thereof, which each show excellent adhesion to the mucous membrane in the oral cavity. Examples of such preparations include solid preparations for oral use such as the high-viscosity gel containing a carboxyvinyl polymer and a hydroxypropylmethyl cellulose (HPMC) in combination described in JP-A-7 267839. However according to the inventors therein, such conventional preparations still have the problem that the cationic bactericide loses bactericidal activity when used in combination with an anionic ingredient e.g. a carboxyvinyl polymer. According to EP 0 864 315B1, this problem is solved by using a specific hydroxypropyl methyl cellulose which is incorporated as a thickener into the liquid oral preparation. Apparently such a preparation adheres well to oral tissues, especially to the surfaces of teeth. The Examples in EP 0 864 315B1 include comparative examples of formulations that comprise alternative cellulose ether thickeners to HPMC. The alternative cellulose thickeners investigated alongside the cationic bactericide, cetyl pyridinium chloride, include hydroxethyl cellulose, hydroxypropyl cellulose and methyl cellulose.

US2004/0062724 (Daniel G. Moro et al) discloses a further alternative means of delivering an active compound to teeth surfaces. US2004/0062724 discloses an erodible multilayered strip comprising at least two layers, a first layer comprising a water-soluble polymer or a combination of polymers that adheres to moist enamel surfaces and a second non-adhesive backing layer that is water-erodible and controls the residence time of the strip. The adhesive polymers are disclosed as being any water-soluble FDA approved polymers for oral applications that stick to an enamel surface when in contact with a moist tooth surface. The adhesive polymers may comprise hydroxyethyl cellulose, hydroxypropyl cellulose, hydroxypropylmethyl cellulose, hydroxymethyl cellulose, sodium carboxymethyl cellulose, polyvinyl pyrrolidone, polyvinyl alcohol, polyethylene glycol, polyacrylic acid, polyethylene oxide alone or in combination thereof. The preferred adhesive polymers are hydroxyethyl cellulose and polyvinyl pyrrolidone.

According to the present invention there is provided an oral care composition comprising hydroxypropyl cellulose, which serves to increase delivery of an active agent to soft tissues and related surfaces in the oral cavity.

SUMMARY OF THE INVENTION

In one aspect the invention provides an oral care composition which is a liquid at or below room temperature and which forms a two-phase cloudy system at body temperature and wherein the composition comprises an active agent and hydroxypropyl cellulose having a cloud point in the composition at about 32° to 38° C.

The present invention is based upon the unexpected finding that a certain type of the cellulose ether polymer, hydroxypropyl cellulose, can enhance delivery of an active agent to mucosal cells/soft tissue in the oral cavity. The present inventors have demonstrated that a composition according to the invention provides enhanced uptake of an active agent by mucosal cells, relative to a control composition which does not contain the hydroxypropyl cellulose. Unlike the control composition, a composition according to the invention has the property of being both a liquid at room temperature and of forming a cloudy suspension when warmed to body temperature. Whilst not being bound by any theory, it is believed that such a property can be utilised for delivery of active agents. Advantageously an active agent can be introduced in the body as a solution and then be effectively delivered to mucosal tissue just by means of increase in temperature. The mucosal tissue may then act as a reservoir for delivery of active agent(s) to the oral cavity as a whole.

DETAILED DESCRIPTION OF THE INVENTION

A composition according to the invention comprises the water-soluble, non-ionic polymer hydroxypropyl cellulose (HPC). There are a number of different grades of HPCs available commercially of varying degrees of polymerisation and molecular weight. Suitably grades of HPC having a low molecular weight i.e. an average molecular weight (M.W.) falling within the range of from about 80,000 to about 370,000 may be used. One suitable brand is Klucel® marketed by Aqualon, a division of Hercules Incorporated, and available from Hercules Incorporated, Aqualon Division, Hercules Plaza, 1313 North Market Street, Wilmington, Del. 19894-0001, USA. Suitable examples include Klucel GF, Klucel JF, Klucel LF and Klucel EF and mixtures thereof. Klucel GF has a viscosity in the range 150-400 mPa s at a 2% concentration at 25° C. and a molecular weight of about 370,000; Klucel JF has a viscosity in the range 150-400 mPa s at a 5% concentration at 25° C. and a molecular weight of about 140,000; Klucel LF has a viscosity in the range 75-150 mPa s at a 5% concentration at 25° C. and a molecular weight of about 95,000; and Klucel EF has a viscosity in the range 200-600 mPa s at a 10% concentration at 25° C. and a molecular weight of about 80,000. For more details on viscosity determinations of various grades of HPC, see the Handbook of Pharmaceutical Excipients, Fifth Edition, (2006), pages 336-340. Suitably the HPC for use in the invention is used in an amount ranging from 0.1 to 10% by weight of the composition, such as 1 to 5%.

Whilst EP 0 558 586 B1 discloses compositions comprising water-soluble, non-ionic cellulose ethers having a cloud point no higher than 40° C., such ethers are not suitable for use herein. The compositions according to EP 0 558 856 B1 form a gel (and not a cloudy phase) and are observed to increase in viscosity when warmed to body temperature. In contrast a composition according to the present invention is a liquid that reduces in viscosity when warmed to body temperature.

By "cloud point" (CP) is meant herein the temperature at which a transparent aqueous solution of hydroxypropyl cellulose becomes cloudy and bulk phase separation starts. Whilst not being bound by any theory, phase separation occurs when polymer-water interactions become less favourable, for example as may occur when temperature is increased e.g. from room temperature to body temperature. Cloud point may be visually observed by observing the temperature at which an aqueous solution of the hydroxypropyl cellulose becomes cloudy or turbid. Alternatively since phase separation results in a lowering of viscosity, rheological techniques may also be employed to determine cloud point. For example by carrying out a temperature-viscosity sweep using an Anton-Paar air bearing rheometer utilising a 50 mm diameter parallel plate (with vapour trap) with 0.3 mm gap, 20/s shear rate and a temperature ramp from 20° C.-45° C.

At room temperature a composition according to the invention is in the form of a homogenous liquid whilst at a higher temperature in the range about 32° to 38° C., more suitably at oral body temperature, the composition undergoes a phase transition to form a two-phase cloudy system with one phase dispersed in the other. In order to be in the form of a homogenous liquid at room temperature or below and in the form of a two-phase cloudy system at body temperature, the hydroxypropyl celluloses of use in the invention have a CP in the composition no higher than about 38° C.

In one aspect a composition according to the invention comprises a cloud point modifying agent. A cloud point modifying agent can be used to shift the intrinsic CP of the hydroxypropyl cellulose to a desired temperature for example from about 45° C. to about 38° C. or below. By "intrinsic CP" is meant the CP in a simple aqueous solution. In one embodiment a cloud point modifying agent shifts the intrinsic CP from about 41° C. to about 32° C.

Suitable cloud point modifying agents include agents that influence solvent quality such as salts or humectants. Suitable salts for use herein include alkali metal salts such as sodium chloride. Suitable salts may be used in an amount ranging from 0.1 to 10%, typically from 0.5 to 5% by weight of the composition.

Suitable humectants for use herein include those selected from glycerine, sorbitol, xylitol, propylene glycol, polyethylene glycol and mixtures thereof. Suitable humectants may be used in an amount ranging from 1 to 30%, typically from 2 to 15% by weight of the composition.

In one aspect a composition according to the invention includes one or more active agents or a mixture thereof. Examples of active agents include a mineralizing agent, an anti-caries agent, an anti-inflammatory agent, an antibacterial agent, an antifungal agent, an anti-malodour agent and mixtures thereof. It will be recognized that some active agents may have more than one therapeutic role. For example zinc ions are known for use as an antibacterial agent, as well as for combating oral malodour, and fluoride ions are known for use as both a mineralizing agent and as an anti-caries agent.

In one embodiment according to the invention the active agent comprises a mineralizing agent comprising a source of fluoride ions. Fluoride ions help promote the remineralisation of teeth and to increase the acid resistance of dental hard tissues for combating caries, dental erosion (i.e. acid wear) and/or tooth wear. Suitable sources of fluoride ions for use in the invention include an alkali metal fluoride such as sodium fluoride, an alkali metal monofluorophosphate such a sodium monofluorophosphate, stannous fluoride, or an amine fluoride in an amount to provide from 25 to 3500 ppm of fluoride ions, preferably from 50 to 500 ppm. A typical fluoride source is sodium fluoride, for example the composition may contain 0.01 to 0.1% by weight of sodium fluoride, e.g. 0.0553% by weight (equating to 250 ppm of fluoride ions).

In one embodiment according to the invention the active agent comprises a mineralizing agent comprising a source of calcium ions. Suitably the source of calcium ions is a calcium salt such as calcium chloride, calcium lactate, calcium gluconate, calcium nitrate, calcium acetate, calcium bicarbonate, calcium sulphate, calcium malate, calcium maleate, calcium tartrate and calcium chloride. Suitably the calcium salt is present in an amount ranging from about 0.02 to 2% by weight of the composition, for example 0.05 to 1% by weight of the composition.

In an alternative embodiment according to the invention the active agent comprises a mineralizing agent comprising a source of fluoride ions and a source of calcium ions. In such an embodiment, the source of fluoride ions will not adversely interact with the source of calcium ions. In some embodiments comprising a source of fluoride ions and a source of calcium ions, the source of fluoride ions may comprise, for example, sodium monofluorophosphate in preference to sodium fluoride.

In one embodiment according to the invention the active agent comprises an anti-inflammatory agent such as a non-ionic anti-inflammatory compound. Examples of such compounds include vitamin compounds; curcuminoids; oils and extracts from spices and botanicals; oils and extracts from thyme, oregano and sage; neem oil; flavonoids and flavones; phenolics from plant sources and IPMP (also known as 4-isopropyl 3-methylphenol, biosol or p-thymol).

In one embodiment according to the invention the active agent comprises IPMP. Suitably the IPMP is present in an amount from 0.005% to 0.50%, for example from 0.01% to 0.20% or 0.02% to 0.10% by weight of the composition.

In one embodiment according to the invention the active agent comprises an antibacterial agent such as a nonionic or a cationic antibacterial compound or a mixture thereof. Examples of nonionic antibacterial compounds include halogenated diphenyl ether compounds such as Triclosan, halogenated carbanilides such as trichlorocarbanilide, and phenolic compounds such as thymol and mixtures thereof. Examples of cationic antibacterial compounds include chlorhexidine digluconate, benzalkonium chloride and cetyl pyridinium chloride. Typically the antibacterial agent will be used in an amount ranging from 0.01 to 0.5% by weight of the composition, for example from about 0.02 to 0.2% by weight of the composition.

In one embodiment according to the invention the active agent comprises an antifungal agent effective in the treatment of oral mycosis. Examples of such antifungal agents include nystatin, clotrimazole, econazole, oxiconazole, ketoconazole, miconazole, cilopirox, amphotericin B and sulconazole. Typically the antifungal agent will be used in an amount ranging from 0.1 to 5% by weight of the composition, for example from about 0.5 to 2.5% by weight of the composition.

In one embodiment according to the invention the active agent comprises a malodour agent such as a source of zinc ions. Suitably the source of zinc ions is a zinc salt such as zinc chloride, zinc citrate, zinc acetate, zinc sulphate, zinc gluconate, zinc salicylate, zinc lactate, zinc malate, zinc maleate, zinc tartrate, zinc carbonate, zinc phosphate, zinc oxide or zinc sulphate. Additional zinc salts are referred to in U.S. Pat. no. 4,022,880 (Vinson et al). Suitably the zinc salt is present in an amount from 0.02% to 2%, for example from 0.05% to 1% by weight of the composition.

Compositions of the present invention contain one or more orally acceptable carriers or excipients. Such carriers and excipients include appropriate formulating agents such as abrasives, surfactants, thickening agents, flavouring agents, sweetening agents, opacifying or colouring agents, pH buffering agents and preservatives, selected from those conventionally used in the oral care composition art for such purposes. Examples of such agents are as described in EP 929287 or WO6/013081.

Oral compositions of the present invention are typically formulated in the form of mouthwashes, sprays, or aqueous solutions for oral trays.

Compositions according to the present invention may be prepared by admixing the ingredients in the appropriate relative amount in any order that is convenient.

The invention is further illustrated by the following Examples:

EXAMPLES

Example 1

Rheology Assessment of HPC Solutions

The following aqueous solutions (Formulas 1-4) were prepared:

| Ingredient | Formula 1 % w/w | Formula 2 % w/w | Formula 3 % w/w | Formula 4 % w/w |
| --- | --- | --- | --- | --- |
| HPC (Klucel JF) | 4.0 | 4.0 | 4.0 | 4.0 |
| Sodium Chloride | — | — | 4.0 | 0.50 |
| Glycerine | — | 20.0 | — | 5.0 |
| PEG-60 Hydrogenated Castor Oil | — | — | — | 1.0 |
| Flavour | — | — | — | 0.20 |
| Sodium Saccharin | — | — | — | 0.05 |
| Cetylpyridium Chloride | — | — | — | 0.05 |
| Methyl paraben | — | — | — | 0.05 |
| Propyl paraben | — | — | — | 0.05 |
| FD&C Blue No 1 | — | — | — | 0.0002 |
| Water | To 100 | To 100 | To 100 | To 100 |

Methods

The viscosity values were determined for Formulas 1-4 using an Anton-Paar air-bearing rheometer, using a 50 mm diameter parallel plate (with vapour trap) with 0.3 mm gap, 20/s shear rate and a temperature ramp of 20° C. to 45° C., following an initial settling period at 20° -30° C.

Results

The results of the effects of increasing temperature on the viscosity of aqueous solutions of HPC are shown in Table 1 below. The influence of the addition of salt and humectant on the viscosity is also shown.

TABLE 1

Temperature vs. Viscosity

| | Temperature ° C. | | | | | | | | |
|---|---|---|---|---|---|---|---|---|---|
| | 20.0 | 25.0 | 30.0 | 32.5 | 35.0 | 37.5 | 40.0 | 42.5 | 45.0 |
| Formula1 (viscosity mPa · s) | 107 | 93 | 79 | 73 | 69 | 67 | 63 | 55 | 23 |
| Formula 2 (viscosity mPa · s) | 229 | 197 | 166 | 150 | 122 | 90 | 22 | 11 | 8 |
| Formula 3 (viscosity mPa · s) | 139 | 124 | 111 | 76 | 12 | 5 | 4 | 5 | 6 |
| Formula 4 (viscosity mPa · s) | 74 | 65 | 54 | 44 | 36 | 14 | 5 | 2 | 2 |

Conclusions

The viscosity of the solution containing polymer alone decreases slowly with temperature until around 42.5° C. when a significant drop is observed resulting from the polymer phase transition, upon reaching its cloud point. The other formulations show this viscosity drop at lower temperatures as a result of a shift in the cloud point and the corresponding phase transition resulting in precipitation of the polymer.

Example 2

Visual Determination of Cloud Point

The following additional aqueous solutions (Formulas 5-11) were prepared:

| Ingredient | Formula 5 % w/w | Formula 6 % w/w | Formula 7 % w/w | Formula 8 % w/w | Formula 9 % w/w | Formula 10 % w/w | Formula 11 % w/w |
|---|---|---|---|---|---|---|---|
| HPC (Klucel LF) | — | — | 2.0 | — | — | — | — |
| HPC (Klucel JF) | 2.0 | 4.0 | — | — | 4.0 | 4.0 | — |
| HPC (Klucel GF) | — | — | — | 1.0 | — | — | — |
| Sodium Chloride | 4.0 | 4.0 | 4.0 | 4.0 | 0.50 | 0.50 | 0.50 |
| Glycerine | — | — | — | — | 5.0 | 5.0 | 5.0 |
| PEG-60 Hydrogenated Castor Oil | | | | | | | |
| Flavour | — | — | — | — | 1.0 | 1.0 | 1.0 |
| Sodium Saccharin | — | — | — | — | 0.20 | 0.20 | 0.20 |
| Cetylpyridium Chloride | — | — | — | — | 0.05 | 0.05 | 0.05 |
| Methyl paraben | — | — | — | — | — | 0.05 | — |
| Propyl paraben | — | — | — | — | — | 0.05 | — |
| FD&C Blue No 1 | — | — | — | — | — | 0.05 | — |
| Water | — | — | — | — | 0.0002 | 0.0002 | 0.0002 |
| | To 100 | To 100 | To 100 | To 100 | To 100 | To 100 | To 100 |

Cloud Point Determination

The cloud point was determined by equilibration of the samples in a water bath at the chosen temperatures. The samples were visually inspected and the temperature where the samples became turbid was recorded.

Results

The results are shown in Table 2 below.

TABLE 2

Cloud points for formula examples

| | | Observations | | | | | | |
|---|---|---|---|---|---|---|---|---|
| Formula | Mw HPC | 22° C. | 25° C. | 28° C. | 30° C. | 32° C. | 35° C. | 37° C. |
| 1 | 140000 | Clear | Clear | Clear | Clear | Clear | Clear | Clear |
| 2 | 140000 | Clear | Clear | Clear | Clear | Clear | Cloudy | Cloudy |
| 3 | 140000 | Clear | Clear | Clear | Clear | Cloudy | Cloudy | Cloudy |
| 4 | 140000 | Clear | Clear | Clear | Clear | Cloudy | Cloudy | Cloudy |
| 5 | 140000 | Clear | Clear | Clear | Clear | Cloudy | Cloudy | Cloudy |
| 6 | 140000 | Clear | Clear | Clear | Clear | Cloudy | Cloudy | Cloudy |
| 7 | 95000 | Clear | Clear | Clear | Clear | Cloudy | Cloudy | Cloudy |
| 8 | 370000 | Clear | Clear | Clear | Clear | Clear | Cloudy | Cloudy |
| 9 | 140000 | Clear | Clear | Clear | Clear | Clear | Cloudy | Cloudy |
| 10 | 140000 | Clear | Clear | Clear | Clear | Cloudy | Cloudy | Cloudy |
| 11 | N/A | Clear | Clear | Clear | Clear | Clear | Clear | Clear |

Conclusions

The results show that when compared to the solutions containing no HPC or HPC alone the cloud points observed are lower. This occurs with a range of HPC concentrations and molecular weights and demonstrates the influence of the inclusion of the formula components.

Example 3

Tissue Retention Testing

The following additional aqueous solutions (Formulas 12-17) were prepared:

| Ingredient | Formula 12 % w/w | Formula 13 % w/w | Formula 14 % w/w | Formula 15 % w/w | Formula 16 % w/w | Formula 17 % w/w |
|---|---|---|---|---|---|---|
| HPC (Klucel JF) | — | 2.0 | 4.0 | — | 2.0 | 4.0 |
| Sodium Chloride | 0.50 | 0.50 | 0.50 | — | — | — |
| Glycerin | 5.0 | 5.0 | 5.0 | 5.0 | 5.0 | 5.0 |
| PEG-60 Hydrogenated Castor Oil | 1.0 | 1.0 | 1.0 | 0.75 | 0.75 | 0.75 |
| Flavour | 0.20 | 0.20 | 0.20 | 0.15 | 0.15 | 0.15 |
| Sodium Saccharin | 0.05 | 0.05 | 0.05 | 0.05 | 0.05 | 0.05 |
| Sodium Citrate | — | — | — | 0.50 | 0.50 | 0.50 |
| IPMP | 0.05 | 0.05 | 0.05 | — | — | — |
| Zinc Chloride | — | — | — | 0.10 | 0.10 | 0.10 |
| Sodium Fluoride | — | — | — | 0.0553 | 0.0553 | 0.0553 |
| FD&C Blue No 1 | 0.0002 | 0.0002 | 0.0002 | 0.0002 | 0.0002 | 0.0002 |
| Water | To 100 | To 100 | To 100 | To 100 | To 100 | To 100 |

Methods

Human Gingival tissues (3D Epigingival tissues obtained from Matek Corporation) were used to investigate the retention of the following actives: 4-isopropyl-3-methylphenol (IPMP), fluoride (as sodium fluoride) and zinc (as zinc chloride).

Retention testing was carried out independently for each active being investigated. 100 ul of treatment was added directly on top of the tissues removed from a 37° C. incubator and tissue plates were then placed immediately back in the incubator. After 1 min contact time of treatment on tissues, plates were removed and the treatment was aspirated off and tissues were washed briefly in autoclaved deionised sterile water. This process was repeated a further 3 times (i.e. total of 4 tissue treatments). Each treatment regime was carried out in triplicate.

Following tissue treatments, the tissues were harvested by carefully cutting the tissues from their plastic inserts and placing the tissues in the appropriate extraction buffer. For IPMP analysis, the tissues were placed in 1 ml of 50:50 DI water:methanol solution.

For zinc analysis, tissues were placed in 5 mls of 5% nitric acid, and fluoride tissues were placed in 1 ml of 18.2 Ohm water.

Each sample was then sonicated for 15 minutes. Following sonication, a sample aliquot was transferred to a glass vial and centrifuged at 2000 rpm for 2 minutes. Supernatants were then transferred to HPLC vials for analysis and then stored at 2-8° C. until analysis was carried out.

The amount of fluoride ion retained was calculated following analysis by a standard Ion Chromatography technique.

The amount of IPMP retained was calculated following analysis by a standard HPLC (High Performance Liquid Chromatography) technique.

The amount of Zinc retained was calculated following analysis by a standard AAS (Atomic Absorbtion Spectroscopy) technique.

Results

The results are shown in Table 3 below.

TABLE 3

Cell Uptake of Active Materials

| Formula | HPC (% w/w) | Material | Cell Uptake (μg/tissue) | SE (n = 3) |
|---|---|---|---|---|
| 12 | 0 | IPMP | 0.20 | 0.018 |
| 13 | 2 | IPMP | 0.75 | 0.24 |
| 14 | 4 | IPMP | 1.19 | 0.12 |
| 15 | 0 | Zinc Ion | 1.26 | 0.10 |
| 16 | 2 | Zinc Ion | 1.78 | 0.34 |
| 17 | 4 | Zinc Ion | 2.82 | 0.30 |
| 15 | 0 | Fluoride Ion | 0.022 | 0.0091 |
| 16 | 2 | Fluoride Ion | 0.020 | 0.0047 |
| 17 | 4 | Fluoride Ion | 0.046 | 0.0103 |

Conclusions

The results show that the inclusion of HPC significantly enhances the uptake of the non-ionic IPMP, the anionic fluoride ion and the cationic zinc ion to the epigingival tissues.

The invention claimed is:

1. An oral care composition in the form of a mouthwash which is a liquid at or below room temperature and which forms a two-phase cloudy system at body temperature and wherein the composition comprises an active agent comprising IPMP, (4-isopropyl-3-methylphenol) a source of zinc ions, or a source of fluoride ions, and mixtures thereof; and a hydroxypropyl cellulose having an average molecular weight in the range from about 80,000 to about 370,000 and a cloud point in the composition at a temperature in the range 32° to 38° C.

2. An oral care composition according to claim 1 further comprising one or more cloud point modifying agents selected from a salt, a humectant and mixtures thereof.

3. An oral care composition according to claim 2 further comprising a salt, wherein the salt is an alkali metal salt, present in an amount ranging from 0.1 to 10% by weight of the composition.

4. An oral care composition according to claim 2 further comprising a humectant, wherein the humectant is present in an amount ranging from 1 to 30% by weight of the composition.

5. An oral care composition according to claim 1, wherein the source of zinc ions is selected from zinc chloride, zinc citrate, zinc acetate, zinc sulphate, zinc gluconate, zinc salicylate, zinc lactate, zinc malate, zinc maleate, zinc tartrate, zinc carbonate, zinc phosphate, zinc oxide, zinc sulphate and mixtures thereof.

6. An oral care composition according to claim 1, wherein the source of zinc ions is a zinc salt present in an amount ranging from 0.02% to 2% by weight of the composition.

7. An oral care composition according to claim 1, wherein the source of fluoride ions is an alkali metal fluoride, an alkali metal monofluorophosphate, stannous fluoride or an amine fluoride.

8. An oral care composition according to claim 1, wherein the source of fluoride ions is present in an amount ranging from 0.01 to 0.1% by weight of the composition.

9. An oral care composition according to claim 1, wherein the IPMP is present in an amount ranging from 0.005% to 0.50% by weight of the composition.

* * * * *